United States Patent [19]
Coles et al.

[11] Patent Number: 5,547,604
[45] Date of Patent: Aug. 20, 1996

[54] LIQUID CRYSTAL SILOXANES

[75] Inventors: Harry J. Coles, Stockport; Jonathon P. Hannington, Beddau; David R. Thomas, Barry, all of United Kingdom

[73] Assignee: Dow Corning Limited, Barry, Wales

[21] Appl. No.: 386,611

[22] Filed: Feb. 10, 1995

Related U.S. Application Data

[63] Continuation of Ser. No. 185,530, Jan. 21, 1994, abandoned.

[30] Foreign Application Priority Data

Jan. 30, 1993 [GB] United Kingdom ............ 9301883

[51] Int. Cl.$^6$ ............ C09K 19/52; C09K 19/12; C07F 7/04; C07F 7/08
[52] U.S. Cl. .............. 252/299.01; 252/299.66; 556/450; 556/453; 556/454; 556/456
[58] Field of Search ............ 252/299.01, 299.66; 556/450, 453, 454, 456

[56] References Cited

U.S. PATENT DOCUMENTS

| | | | |
|---|---|---|---|
| 4,358,391 | 11/1982 | Finkelmann et al. | 252/299.01 |
| 4,981,607 | 1/1991 | Okawa et al. | 252/299.01 |
| 5,106,530 | 4/1992 | Hans et al. | 252/299.1 |
| 5,138,010 | 8/1992 | Keller et al. | 252/299.01 |
| 5,259,987 | 11/1993 | McArdle et al. | 252/299.01 |
| 5,316,693 | 5/1994 | Yuasa et al. | 252/299.01 |
| 5,354,489 | 10/1994 | Inoue et al. | 552/299.01 |
| 5,455,697 | 10/1995 | Coles et al. | 252/299.01 |

FOREIGN PATENT DOCUMENTS

| | | |
|---|---|---|
| 322703 | 7/1989 | European Pat. Off. . |
| 338576 | 10/1989 | European Pat. Off. . |
| 478034 | 4/1992 | European Pat. Off. . |
| 01144491 | 6/1989 | Japan . |
| 01268785 | 10/1989 | Japan . |
| 02180890 | 7/1990 | Japan . |
| 2146787 | 4/1985 | United Kingdom . |

*Primary Examiner*—Shean C. Wu
*Attorney, Agent, or Firm*—Patricia M. Scaduto

[57] ABSTRACT

Siloxane compounds having a smectic liquid crystal phase and the general formula

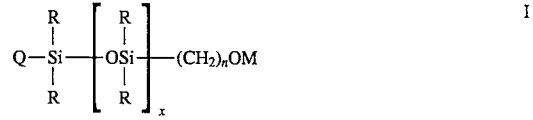

wherein each R=alkyl, alkenyl or aryl, Q represents a monovalent group, for example alkyl, —(CH$_2$)$_n$OM', a chiral organic group, a dye group, a non-linear optic group or the group —(CH$_2$)$_n$L, in which L represents a siloxane group, M and M' each represent

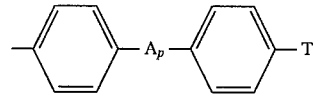

wherein A is carboxyl, T is CN, F or Cl and p=0 or 1, provided that when T is F or Cl x has a value of at least 2.

7 Claims, No Drawings

LIQUID CRYSTAL SILOXANES

CROSS-REFERENCE TO RELATED APPLICATIONS

This is a continuation of application Ser. No. 08/185,530 filed Jan. 21, 1994, now abandoned.

BACKGROUND OF THE INVENTION

1. Field of the Invention

This invention relates to oligomeric siloxane compounds having liquid crystal properties.

2. Background Information

It is well known that monomeric liquid crystals consist of compounds having an elongated or rod-like structure usually with a rigid core. Such molecules, which usually contain a permanent electrical dipole and easily polarisable chemical groups, may exhibit nematic (N), chiral nematic (N,), smectic (S) and chiral smectic (S*) mesophases but on cooling to lower temperatures experience a transition to a solid crystal. This liquid crystal to solid crystal transition destroys the liquid crystalline order. Side chain polymer materials are known which exhibit similar liquid crystalline phases but at lower temperatures undergo a transition from one liquid crystal state to a viscous or glass state thereby storing the liquid crystalline order. Liquid crystal phases, or mesophases, show varying degrees of molecular ordering between the almost perfect three dimensional structure of a crystalline solid which exhibits positional and orientational order and the randomly ordered state of an isotropic fluid.

In the nematic phase (N) all positional order is lost so that the centres of mass of the molecules are arranged randomly in space. The orientational order is, however, maintained so that there is a statistical orientational ordering of the molecules parallel to their long axes. Such phases may have the direction of their alignment altered by the application of mechanical, electrical, optical or magnetic fields. The ability to switch the direction of the alignment gives rise to a display or device element that can be used, for example to display information. Liquid crystal display elements based on the nematic phase are widely used in electro-optical devices such as the displays of digital wrist watches, calculators, word processors, personal computers and the like. However, the nematic liquid crystal material presently used in these displays has problems in terms of its bistability or memory property and of its inapplicability to a high speed switching element.

In the chiral nematic (N*), or cholesteric, mesophase the molecular order is characterised by an orientational order similar to that found in nematics but in this phase the axis direction changes continuously along an axis perpendicular to the first and traces out a helical path. This mesophase requires that the mesogenic material is optically active or contains optically active additives to produce the twisted or chiral nematic mesophase. If the pitch of the helix is of the order of the wavelength of visible light then a characteristic of this N* phase is a bright selective colour reflection. Such chiral nematic mesophases are often used in thermography since slight temperature changes distort the helical pitch and this leads to a change in colour of the reflected, and therefore also, transmitted light.

In a smectic phase the molecular order is characterised by orientational order and two degrees of directional order giving rise to a lamellar structure. Within this broad phase class there are many types of smectic phases depending on whether the centres of mass of the molecules in each layer are randomly arranged (as in a $S_A$ phase) or ordered between themselves (as in a $S_B$ phase) whether the lamellar layers are correlated or whether the orientational order is tilted at some angle to the layer normal as might be the case for a $S_C$ phase. Smectic phases may be aligned in electrical, magnetic or optical fields to give devices with a memory or information storage capability. In the case of low molar mass compounds this in electrical, magnetic, mechanical or optical fields to give devices with a memory or information storage capability. In the case of low molar mass compounds this memory effect is mechanically fragile whilst in the case of polymers the memory is robust but the response time is much slower.

In a chiral smectic phase ($S_C$*) the orientational order is normally inclined to the layer normal, as in a $S_C$ phase, but the direction of the orientation changes continuously along the axis of the layer normal thereby tracing out a helical path rather like a corkscrew. Various chiral smectic phases exist depending on the type of orientational order within the layer. Such chiral mesophases normally exhibit ferroelectric properties and it is known that a liquid crystal display element containing such a chiral mesophase, a so-called ferroelectric, is capable of high speed response, in the order of 10 microseconds, and has a memory property.

Low molar mass liquid crystals having chiral and nonchiral nematic or smectic structures are known and because of their optical and electrical properties have found many technological uses especially in the opto-electronics field. However, the known materials have some limitations on their performance which restricts their ultimate applicability.

Recently much work has gone into the study of low molar mass (LMM) liquid crystals with electro-optic properties suitable for use at ambient temperatures. Since one highly desirable property was fast electro-optic switching, and because this switching time depends on the cooperative molecular reorientation, attention was focussed on the synthesis of relatively small molecules of low mean viscosity. However, despite the wide range of materials prepared it is only quite recently that electro-optic devices have become firmly established with the discovery of the cyanobiphenyl family of compounds. At lower temperatures these compounds exhibit crystalline phases which limit their response time in the mesomorphic phase and destroy the induced order on cooling from the said mesophase to the crystalline phase. Although LMM liquid crystals have been used for storage of the induced order in, for example a smectic phase, there are a number of disadvantages as follows:

1. the stored information in the smectic phase is often easily lost by mechanical or thermal stress;

2. cooling into the inherent crystal phase destroys the induced order;

3. grey scaling which is the production of different degrees of controlled light transmission or scattering is difficult, and 4. difficulties arise in controlling the alignment on cooling from the isotropic phase since the materials generally prefer to align homeotropically, that is perpendicular to the substrate, rather than predominantly parallel in a high optical contrast scattering state.

Having regard to these disadvantages there exists a need for improvement in such materials.

It is therefore an object of the present invention to provide novel low mass liquid crystal materials having siloxane-containing structures and mixtures containing them, that may be incorporated into a wide variety of opto-optic, magneto-optic, electro-optic and mechanical or thermo-optic storage and non-storage devices.

Siloxane-containing liquid crystal polymers in which the mesogen is present as a side chain have been disclosed in U.S. Pat. No. 4,358,391 and GB 2 146 787B. Siloxane-containing liquid crystals have been disclosed in EP-A-0 322 703 which relates to a liquid crystal composition comprising a main chain-type mesomorphic polymer and a mesomorphic monomer and showing a smectic phase. EP-A-0 478 034 relates to a homogeneous electro-rheological fluid which mainly comprises a liquid crystal compound in which a plurality of liquid crystal groups are bonded to a molecular chain, or comprises a lyotropic liquid crystal comprising a solute and a solvent. The liquid crystal compound may have a siloxane molecular chain. Siloxane-containing chiral smectic liquid crystals are disclosed in JP 01144491 and JP 01268785 and nematic siloxane-containing liquid crystals are disclosed in JP 02180890.

SUMMARY OF THE INVENTION

According to the present invention there are provided siloxane compounds having a smectic liquid crystal phase and represented by the general formula

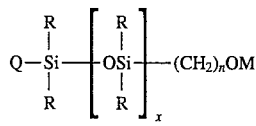    I wherein each R represents an alkyl group having from 1 to 12 carbon atoms, an alkenyl group having from 1 to 6 carbon atoms or an aryl group having from 6 to 12 carbon atoms, Q represents a monovalent group selected from alkyl groups having from 1 to 8 carbon atoms, $-(CH_2)_nOM'$, a chiral organic group, a dye group, a non-linear optic group or the group $-(CH_2)_nL$, in which L represents a group selected from the $R_3Si[OR_2Si]y-$ and

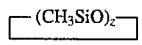

groups in which each R is as defined hereinabove, each of the remaining free valencies of silicon is satisfied by the group $-(CH_2)_nSiR_2[OSiR_2]_x(CH_2)_nOM$, y is an integer from 1 to 4 and z is an integer from 4 to 6, x is an integer from 1 to 10, each n is an integer from 4 to 11 and each M and M', which may be the same or different, represents a mesogenic group having the general formula

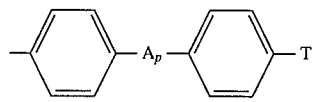    II wherein the linkage A is selected from

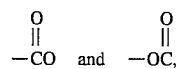

T represents CN, Cl or F and p is 0 or 1 provided that when T is F or Cl x has a value of at least 2.

DETAILED DESCRIPTION OF THE INVENTION

Depending on the meaning given to Q the general formula I represents a molecule having or containing an AB or BAB configuration wherein B represents the organic mesogenic moiety and A represents the siloxane portion. For example when Q is alkyl, alkenyl or aryl the molecule will have the AB structure. When Q represents the group $-(CH_2)_nOM'$ the molecule will be of the BAB configuration. When L represents

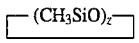

the molecule will consist of a plurality of AB structures linked to a cylic siloxane.

In the general formula hereinabove the R groups are preferably n-alkyl containing 1 to 5 carbon atoms, the preferred terminal group T is CN and the preferred ranges of x and n are from 1 to 4 and from 6 to 11 respectively.

The siloxane-containing liquid crystals of the invention can be prepared by the reaction between a diorganosiloxane oligomer having not more than 11 silicon atoms and a hydrogen atom bonded to one or both terminal silicon atoms and an alkenyl-terminated mesogen in the presence of a suitable hydrosilylation catalyst, for example a platinum compound or complex. This is represented schematically below for the AB and BAB cases

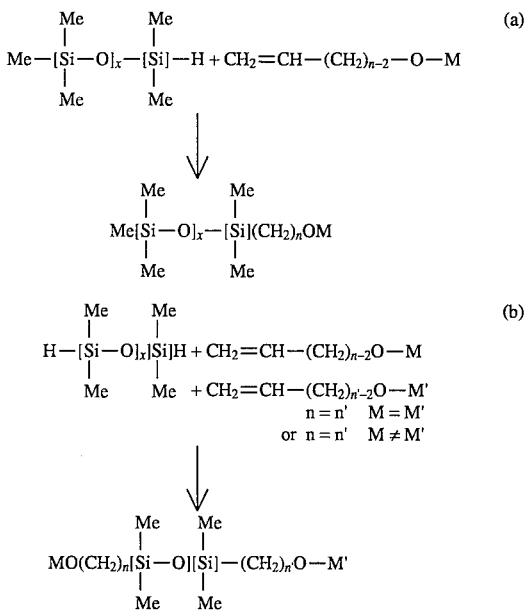

When L represents the cyclic siloxane structure

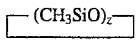

the liquid crystal may be prepared by first reacting a methylalkenyl, for example methylvinyl, cyclic siloxane with a siloxane oligomer, for example tetramethyldisiloxane, having terminal silicon-bonded hydrogen under conditions whereby one SiH per molecule reacts with each alkenyl group. The product is then reacted with the mesogen having terminal unsaturation in the manner illustrated above.

The siloxane-containing liquid crystals of this invention can be characterised for their structure and phase types employing known techniques, for example $^{29}Si$ nmr, x-ray scattering, optical microscopy, differential scanning calorimetry, dielectric relaxation, rheology and optical spectroscopy. The introduction of the siloxane unit acts to suppress the crystalline phase of the mesogenic structural elements and can replace them by a glass phase with a very low glass transition temperature $T_g$ thereby improving the response times. Further it has been discovered that the smectic phases have an enhanced structural order that has improved the resistance to mechanical shock and may serve to improve the grey-scaling capability.

In one embodiment of the invention the group Q may contain a dye moiety. This dye moiety may be pleochroic, fluorescent or optically non linearly active, thereby allowing coloured and/or functional materials to be produced. Equally such dye structures chemically linked to the siloxane-containing molecules or not may be included as guest into liquid crystalline host. Preferred dyes as guests are for example anthraquinone, azo or perylene structures.

An advantage of the siloxane compounds of this invention is that they exhibit smectic phases without requiring the additional presence of other liquid crystal materials. However, if desired, they may be mixed between themselves or with other low molar mass or polymeric liquid crystals to improve or otherwise modify bulk properties. They may for example be mixed with known low molar mass (LMM) liquid crystals. When used this way they may usefully modify the elastic constants, viscosity coefficients and optical and dielectric properties of the LMM materials. When mixtures of these types are made improvements can be made to the operating temperature range, the viscosity and the multiplexibility. It is preferred that when used this way the LMM material contains at least one compound having the same or a closely related structural group to M and/or M', for example when M is

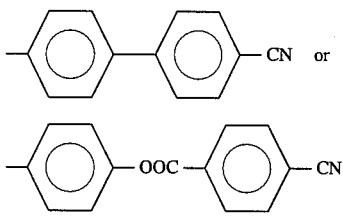

then a preferred liquid crystal liquid material contains compounds such as those described in British Patent 1 433 130 for example of general formula

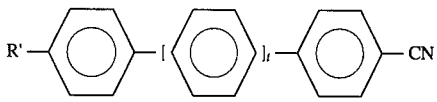

III where t=0 or 1 and R' is alkyl or alkoxy, or the siloxane side chain polymers of the type disclosed in GB-A-2 146 787.

The liquid crystal materials of this invention find application in a variety of devices employing a liquid crystal display. In the most common display type the smectic material is disposed between a pair of substrates which may be of glass or a suitable polymeric material. The inner surfaces are coated with a transparent conducting film, for example indium tin oxide, and an aligning agent. The thickness of the liquid crystal material, usually 1 to 100 μm is defined by spacers which may be for example polymeric films, glass fibres, microbeads or may be photoetched. The conducting film may cover the whole of the inner surface of the substrates or may be etched into a suitable pattern such as a dot matrix or seven segment display. Regions of the film may then be addressed by electrical, magnetic or thermal (e.g. laser) means to effect a change in texture of the material and thereby display the required information. It has been found that in both the clear and light scattering states the siloxane-containing liquid crystals of this invention are particularly resistant to mechanical shock.

It has been further discovered that combinations of fields may be applied, such as electrical and thermal, to allow selective erasure and storage of information so that the materials are particularly suited for optical data recording and storage applications. The thermal source may be a low powered laser and it has been found that suitable choice of laser energy and/or electric field allows grey scale to be achieved.

The following Examples illustrate the invention.

EXAMPLE 1

The compound 4-cyano-4'-hexenyloxybiphenyl (3.40 g), prepared by the reaction of 6-bromohex-1-ene with 4-cyano-4'-hydroxybiphenyl, was charged to a 2-necked round bottom flask fitted with stirrer, dropping funnel, nitrogen purge and reflux condenser. To the flask was also added toluene (45.0 ml) and, as catalyst, a complex formed between divinyltetramethyldisiloxane and chloroplatinic acid. The catalyst was added in sufficient quantity to provide $8.8 \times 10^{-5}$ moles Pt (as metal) per mole of SiH in the pentamethyldisiloxane reactant. The mixture was then heated to 55° C. at which temperature pentamethyldisiloxane (2.00 g, 10% excess SiH to mesogen) was added from the dropping funnel over a period of 30 minutes. A slight exotherm occurred. The mixture was maintained at 60° C. for one hour and then raised to reflux temperature for a further 24 hours.

When the reaction mixture had cooled the toluene and excess siloxane were removed employing a rotary evaporator to leave the compound

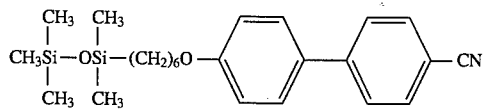

Purification was effected by dissolving the compound in hexane. The insoluble unreacted mesogenic compound was removed by filtration and the hexane then removed by volatilisation at elevated temperature.

Analysis of the oligomeric product by infra-red spectroscopy indicated disappearance of the SiH peak at 2180 cm$^{-1}$. The product was examined by conventional differential scanning calorimetry and polarising microscope techniques to investigate the formation and nature of a mesophase. For the microscopic examination the sample was placed btween two glass slides with a fixed spacing (7 μm) and subjected to several heating and cooling cycles, the change of temperature being controlled at a rate of 2° C. per minute. A smectic A phase was observed up to 43.8° C. and the sample became isotropic at 48.9° C.

EXAMPLE 2

Employing the procedures described in Example 1 pentamethyldisiloxane was reacted with 4-cyano-4'-decenyloxybiphenyl (4.10 g), prepared by the reaction of 10-bromodec-1-ene with 4-cyano-4'-hydroxybiphenyl.

The product

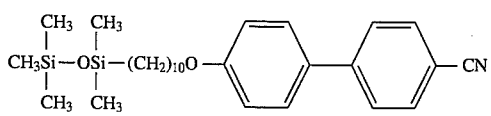

was purified as described in Example 1 and examined by DSC and polarising microscope. The product exhibited a smectic A phase in the range 39.4° C. to 47.5° C. and became isotropic at 61.3° C.

EXAMPLE 3

The procedure of Example 1 was repeated except that the pentamethyldisiloxane was replaced with 1,1.1.3.3.5.5-heptamethyltrisiloxane (3.00 g, 10% excess SiH to mesogen). After purification of the product it was found to exhibit a smectic A phase up to 45° C. and became isotropic at 58° C.

EXAMPLE 4

Employing the procedure of Example 1, 4-cyano-4'-hexenyloxybiphenyl (4.19 g) was reacted with 1.1.3.3.5.5.7.7.9.9-decamethylpentasiloxane (3.00 g, 1:1 ratio SiH to mesogen).

After purification the product

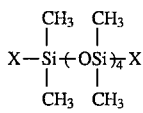

where X=

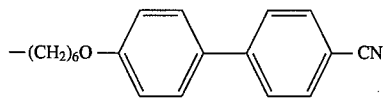

showed a smectic A phase up to 46.5° C. and became isotropic at 56.7° C.

EXAMPLE 5

The procedure of Example 1 was repeated to react together 4-cyano-4'-decenyloxybiphenyl (14.90 g) and tetramethyldisiloxane (3.00 g, 1:1 ratio SiH to mesogen). Purification was carried out by dissolving the reaction product in dichloromethane, adding methanol, separating the methanol layer and finally volatilising the dichloromethane at elevated temperature.

The purified product

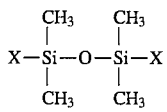

where X=

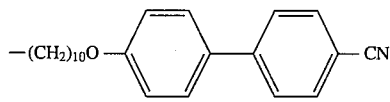

showed a smectic A phase up to 99.4° C. and became isotropic at 102.1° C.,

That which is claimed is:

1. A siloxane compound having a smectic liquid crystal phase and represented by the general formula

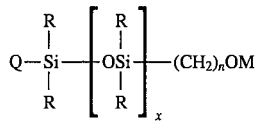

wherein Q represents a monovalent group selected from alkyl groups having from 1 to 8 carbon atoms, —(CH$_2$)$_n$OM', a dye group, or the group —(CH$_2$)$_n$L in which L is

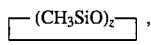, the remaining free valence of each silicon in

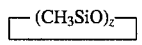

is satisfied by the group —(CH$_2$)$_n$SiR$_2$[OSiR$_2$]$_x$(CH$_2$)$_n$OM and z is an integer from 4 to 6, each x is an integer from 1 to 10, each R represents a group selected from an alkyl group having from 1 to 12 carbon atoms, alkenyl groups having from 2 to 6 carbon atoms and aryl groups having from 6 to 12 carbon atoms, each n is an integer from 6 to 11 and each M and M', which may be the same or different, represents a mesogenic group having the general formula

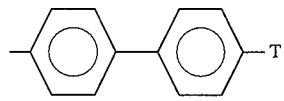

wherein T represents —CH, Cl or F, provided that when T is F or Cl, x has a value of at least 2.

2. A siloxane compound of claim 1, wherein Q represents a group selected from alkyl groups having from 1 to 8 carbon atoms, a dye group and the group —(CH$_2$)$_n$L.

3. A siloxane compound of claim 1, wherein T represents the —CN group.

4. A siloxane compound of claim 1, wherein Q represents the group —(CH$_2$)$_n$OM'.

5. A siloxane compound of claim 3, wherein Q is methyl.

6. A siloxane compound of claim 1, wherein x has a value from 1 to 4.

7. Siloxane compounds of claim 1, wherein R is methyl.

* * * * *